United States Patent [19]
Tao

[11] Patent Number: 5,830,152
[45] Date of Patent: Nov. 3, 1998

[54] PENCIL-GRIP FINE NEEDLE ASPIRATION SYRINGE HOLDER

[76] Inventor: Liang-Che Tao, 957 Ashton Pl., Carmel, Ind. 46033

[21] Appl. No.: 804,609

[22] Filed: Feb. 24, 1997

[51] Int. Cl.$^6$ ........................................................ A61B 5/00
[52] U.S. Cl. ............................. 600/562; 604/19; 604/48; 604/227; 600/578; 600/576
[58] Field of Search ..................... 604/187, 232, 604/227, 19, 48; 128/765, 749, 763, 766, DIG. 1; 600/218, 181, 573, 576, 578

[56] References Cited

U.S. PATENT DOCUMENTS

| | | | |
|---|---|---|---|
| D. 337,821 | 7/1993 | Tan ........................................ | D24/146 |
| 4,333,456 | 6/1982 | Webb .................................... | 128/218 R |
| 4,333,457 | 6/1982 | Margulies ............................. | 128/218 R |
| 4,333,458 | 6/1982 | Margulies et al. ................... | 128/218 R |
| 4,594,073 | 6/1986 | Stine ..................................... | 604/187 |
| 4,605,011 | 8/1986 | Naslund ................................ | 128/752 |
| 4,697,600 | 10/1987 | Cardenas et al. ..................... | 128/753 |
| 4,982,739 | 1/1991 | Hemstreet et al. ................... | 128/750 |
| 5,060,658 | 10/1991 | Dejter, Jr. et al. .................... | 128/753 |
| 5,115,816 | 5/1992 | Lee ........................................ | 128/749 |
| 5,199,441 | 4/1993 | Hogle .................................... | 128/753 |
| 5,241,969 | 9/1993 | Carson et al. ......................... | 128/753 |
| 5,246,011 | 9/1993 | Caillouette ............................ | 128/753 |
| 5,330,443 | 7/1994 | Powles et al. ......................... | 604/240 |
| 5,413,115 | 5/1995 | Baldwin ................................ | 128/763 |
| 5,469,860 | 11/1995 | De Santis ............................. | 128/765 |

*Primary Examiner*—Wynn Wood Coggins
*Assistant Examiner*—N. Kent Gring
*Attorney, Agent, or Firm*—Locke Reynolds

[57] ABSTRACT

A pencil-grip fine needle aspiration syringe holder for accurately placing a needle into a region using a single hand disposed close to the needle tip in a position of natural function, useable with a standard syringe. A body is provided for receiving a syringe barrel, and a slide is movably mounted to the body for engaging a syringe handle, for movement between a withdrawal position where a syringe plunger is in a compact position and a released position where the plunger is in an extended position. A finger engaging member is fixed to the body for grasping the holder in a pencil-grip manner, and a biasing member is coupled between the body and the slide for urging the slide toward the released position and the plunger toward the extended position. A catch is provided for restraining the slide in the withdrawal position and plunger in the compact position, along with a release for releasing the catch to allow the slide to move away from the withdrawal position and towards the released position, decreasing pressure within the syringe. A limit member is situated for limiting movement of the slide and the plunger toward the extended position. An adjustable regulating member is coupled to the limit member for adjusting the position of the limit member relative to the body.

16 Claims, 8 Drawing Sheets

PENCIL-GRIP FINE NEEDLE ASPIRATION SYRINGE HOLDER

BACKGROUND OF THE INVENTION

1. Field of the Invention

The present invention generally relates to tissue extraction devices, and more particularly to hand-held devices for extracting tissue samples by the technique of fine needle aspiration.

2. Description of the Prior Art

Biopsy devices for fine needle aspiration are well known and are useful for obtaining cytologic specimens for examination to confirm the diagnosis of suspected medical conditions. Such devices are useful in sampling tissue from the breast, the head and neck, lymph nodes, and for some gynecologic conditions. Other applications include lung, prostate, and other soft tissue biopsies.

Generally, biopsy instruments of this type extract samples of tissue through a small needle in the range of 25–20 gauge. A vacuum force is typically usually applied by a standard syringe attached to the needle, while the needle is slightly moved several times in the tissue, utilizing an up-and-down motion. A column of cells is then accumulated in a hollow interior of the needle as the needle is passed multiple times into the defiled region. This procedure can be performed with a syringe alone, or, with the syringe disposed in a syringe holding device.

Syringe holding devices for use with fine needle aspiration have been known in the art for some time. A syringe holding device used to perform this technique should be economical, usable with one hand, and provide excellent material specimens when used correctly. However, disadvantages also exist, in that for many such syringe holders, the user's hand must be placed several centimeters from the tissue to be biopsied. This distance is relatively substantial and makes for difficult needle placement and control, which can lead to inaccuracies.

Furthermore, available devices may produce tension in the hand operating the device, which can also lead to inaccuracy in obtaining fine needle aspiration specimens.

In addition, many syringe holding devices for use with fine needle aspiration are intended to be held by the user in a "pistol-grip." When using such pistol-grip devices, however, movement of the device to produce the up-and-down motion of the needle described above is controlled by the user's arm and shoulder muscles, that is, using large motor movements. Unfortunately, precise and accurate movement of the needle of a syringe is difficult using large motor control of a pistol-grip syringe holding device. Control of a pistol-grip syringe holding device using fine motor skills, such as those of the hand, are generally not possible due to the manner in which such devices are held and operated.

Accordingly, there exists a need in the art for an improved fine needle aspiration syringe holder that will place the user's hand close to the exterior surface of the body containing the material to be sampled, and also will provide a device for use in material aspiration having means to provide a predetermined amount of suction. Additionally, there is a need for a fine needle aspiration syringe holder useable with a single hand disposed in a natural position while the device has a stable platform, and which are capable of movement using fine motor control of the hand. These improvements would be particularly desirable when sampling in confined spaces with compact anatomy, such as in the head and neck where proper placement of aspiration needles is essential.

SUMMARY OF THE INVENTION

In order to aid in the understanding of the present invention, it can be stated in essentially summary form that it is directed to a pencil-grip fine needle aspiration syringe holder that allows a user to accurately place a needle into a target region with minimal error using a single hand, to place the hand relatively close to the needle tip while the hand is in a position of natural function, and to be easily manipulated, yet accommodates use of a standard syringe and allows for cost effective and efficient material sampling by aspiration.

More specifically, the present invention is directed to a fine needle aspiration syringe holder which may be used with a syringe of a well-known type including a barrel, a grip, a plunger having a handle, and a needle assembly disposed generally opposing the handle. The plunger is slidably movable within the barrel between a compact position and an extended position. The needle assembly may utilize a 22 gauge or narrower fine needle. The holder includes a generally elongated body formed of left and right body halves joined together, and is capable of receiving the barrel of the syringe. The holder has a first end and a second end, and is adapted to be held in the manner of a pencil between a thumb and forefinger with the first end proximate to the handle and the second end proximate to the needle. A ring-like finger engaging member may be mounted to a lower wall of the body, proximate to the second end, for facilitating the grasping of the holder in a pencil-grip manner, and a bezel may be mounted to the lower wall proximate to the first end. An upper wall of the body includes an upper wall stepped slot, and is mounted to an arcuate, transverse front wall, a rear wall, and a pair of longitudinal, opposing side walls. Each of the side walls includes a stepped portion proximate to the upper wall stepped slot, with the stepped portions defining a chamfered transverse slot. The body defines an interior chamber between the upper wall, the front wall, the rear wall and the side walls. A longitudinal slot is defined through one of the side walls and a slide orifice is defined through the rear wall.

Transversely disposed within the interior chamber proximate to the front wall is a block, defining opposing block slots. The interior chamber also defines opposing guide slots proximate to the rear wall. Disposed within the interior chamber and mounted between the guide slots is a guide, defining a guide aperture. The diameter of the guide aperture may be chosen to be substantially the same as the diameter of the slide orifice. Located within the interior chamber and slidably disposed within the block slots is a catch lock, defining a pair of spring mounting slots and a catch lock aperture, and having a release button tab. The catch lock aperture includes a larger diameter portion disposed proximate to the release button tab and a smaller diameter portion disposed proximate to the spring mounting slots. The release button is disposed through a release button bore defined through a side wall and proximate to the block slots, and is mounted to the catch lock at the release button tab. A catch lock spring is disposed within the interior chamber, between the block and a side wall, and partially within the spring mounting slots, and bears against the catch lock so that the release button normally extends away from the body.

A slide includes a shaft having an interior end and an opposing exterior end defining a tapped exterior end aperture. A rear holder defines a transverse, chamfered rear holder slot, an arcuate notch, and a countersunk fastener hole, and is mounted to the shaft using a threaded fastener disposed through the fastener hole. The shaft further defines a pair of transverse shaft slots proximate to the interior end, an angled tip, and a shaft step defined adjacent to the angled tip. The maximum diameter of the angled tip may be chosen to be slightly smaller than the diameter of the larger diameter portion of the catch lock but larger than the diameter of the smaller diameter portion. The diameter of the shaft step may be chosen to be slightly less than the diameter of the smaller diameter portion.

A coil slide spring is disposed surrounding the shaft, with the interior diameter of the slide spring chosen to be slightly greater that the diameter of the shaft, and the exterior diameter of the slide spring chosen to be slightly less than the diameter of the slide orifice and the guide aperture, thereby permitting sliding movement of the shaft and the slide spring through the slide orifice and the guide. Transversely and circumferentially mounted to the shaft within the interior chamber at each shaft slot is a retaining ring. A stop, defining a stop aperture and a tapped stop fastener hole, is disposed surrounding the shaft and between the retaining rings, with the diameter of the stop aperture chosen to be slightly greater than the diameter of the shaft. The stop is held in place against movement along the shaft by the retaining rings by selecting the dimension of the stop measured along the shaft to be slightly less than the perpendicular distance between the retaining rings, so that the stop is tightly held therebetween. The stop is further mounted to the shaft by a threaded stop fastener.

A regulating block, defining a regulating block aperture and a tapped regulating block hole, is disposed surrounding the shaft within the interior chamber. The diameter of the regulating block aperture is chosen to be slightly greater than the diameter of the shaft but less than the exterior diameter of the slide spring, so that the shaft is capable of sliding movement through the regulating block while the slide spring bears against the regulating block. A threaded regulating fastener having a regulating knob is provided to adjustably mount the regulating block to the body, with the regulating fastener disposed through the longitudinal slot and threadably engaged within the regulating block hole and the regulating knob bearing against a side wall.

The slide is mounted for sliding movement with respect to the body between a withdrawal position where the plunger is disposed in a compact position, and a released position where the plunger is disposed in an extended position. The plunger is biased towards the released position by a biasing member, such as a slide spring, coupled between the body and the slide for urging the slide toward the released position and plunger toward the extended position.

In use, for a syringe of 10 cc capacity, the plunger may be adjusted to a compact position of approximately 2 cc and the syringe may be removably mounted to the present invention, with the barrel disposed adjacent to the body and through the arcuate front wall, the grip disposed within the transverse slot, and the handle engaged within the rear holder slot with the plunger disposed through the notch. In order for the rear holder slot to align with the handle, the slide is pushed towards the withdrawal position against the urging of the slide spring. As the interior end of the shaft approaches the catch lock, the angled tip partially enters the smaller diameter portion which is aligned with the shaft due to the biasing action of the catch lock spring. As the slide is pushed further towards the withdrawal position, against the urging of the slide spring, the angled tip exerts force on the smaller diameter portion causing the catch lock to slide within the block slots against the urging of the catch lock spring, so that the larger diameter portion becomes aligned with the shaft. Upon alignment of the shaft with the larger diameter portion, continued force exerted on the slide towards the withdrawal position causes the angled tip to slide entirely through the catch lock. As the shaft step is disposed through the larger diameter portion, the biasing force of the catch lock spring causes the catch lock to slide away from the release button bore so that the smaller diameter portion of the catch lock aligns with the shaft. With the diameter of the smaller diameter portion less than the maximum diameter of the angled tip, the shaft and the slide are temporarily locked in place in the withdrawal position. As a result, the catch lock operates to restrain the slide in the withdrawal position and thereby restrain the plunger in the compact position.

The present invention may be held in one hand with the thumb pressing against one side wall adjacent to the release button and the index and middle fingers pressing against the opposing side wall, the ring finger disposed through the finger engaging member and against the little finger, so that the present invention is held in a "pencil" grip. An operator may then insert the needle into a desired region to be aspirated, using the efforts of one hand. Utilizing fine motor control of a pencil-grip, placement and movement of the needle is thereby precisely and accurately controlled.

Upon depression of the release button, for instance by pinching pressure of the thumb, the catch lock slides transversely within the block slots against the urging of the catch lock spring, so that the larger diameter portion of the catch lock slides into alignment with the shaft. As the maximum diameter of the angled tip is less than the larger diameter portion, the shaft and the slide are capable of movement toward the released position as a result of urging of the slide spring. The release button acts to release the catch lock, allowing the slide to move away from the withdrawal position and towards the released position under influence of biasing force of the slide spring, moving the plunger from the compact position toward the extended position and decreasing pressure within the syringe. With the needle placed as desired, aspiration of material from the region may be initiated by depressing the release button so that the plunger is drawn back with respect to the syringe, creating negative pressure within the syringe and causing aspiration of material located near tip of the needle. After movement of the plunger has stopped, aspiration is complete, and the present invention, the syringe and the needle are pulled away from the aspirated region, and aspirated material present within the needle hub and the syringe may be removed and analyzed.

As the slide moves toward the released position under urging of the slide spring, the stop slides within the interior chamber towards the first end as the stop is mounted to the shaft by the retaining rings and the stop fastener. Sliding movement of the stop towards the first end and movement of the slide towards the released position is limited by the regulating block, as the shaft slides through the regulating block until the stop comes into contact with the regulating block. In this way, the stop and the regulating block act as a limit member to intercept the slide between the compact position and the extended position, limiting movement of the slide and the plunger, and limiting low pressure achievable within the syringe, and therefore the suction available for aspiration.

The extent of sliding movement of the slide upon release of the catch lock is governed by the location of the regulating block with respect to the longitudinal slot. The regulating block may be moved to a desired location along the longitudinal slot by adjusting the threaded regulating fastener using the regulating knob, sliding the regulating block to the desired location along the longitudinal slot, and tightening the regulating knob to bear against a side wall. As a result, the regulating fastener with the regulating knob act as an adjustable regulating member coupled to the regulating block, for adjusting the position of the regulating block relative to the body, controlling the low pressure achievable within the syringe.

It is therefore an object of the present invention to provide a pencil-grip fine needle aspiration syringe holder that will effectively and efficiently remove materials, such as removal of cells for cytologic examination.

Another object of the present invention is to provide a pencil-grip fine needle aspiration syringe holder that places the hand in a natural position of function so that the manipulation will be precise and simply achieved.

Another object of the present invention is to provide a pencil-grip fine needle aspiration syringe holder having means to provide a predetermined amount of suction and to further allow the user to relax the hand for accurate and precise manipulation of the present invention.

Another object of the present invention is to provide a pencil-grip fine needle aspiration syringe holder whereby the barrel of the syringe is positioned above the hand, and the user may place the hand relatively close to the tip of the needle and the tissue to be sampled.

Yet another object of the present invention is to provide a pencil-grip fine needle aspiration syringe holder which may easily be adapted to CT guided, stereotactic core guided, or ultrasound guided techniques.

Further objects and advantages of the present invention will be apparent from a study of the following portion of the specification, the claims, and the attached drawings.

DETAILED DESCRIPTION OF THE PREFERRED EMBODIMENT

The following portion of the specification, taken in conjunction with the drawings, sets forth the preferred embodiment of the present invention. The embodiment of the invention disclosed herein is the best mode contemplated for carrying out the invention in a commercial environment, although it should be understood that various modifications can be accomplished within the parameters of the present invention.

Figure 1:
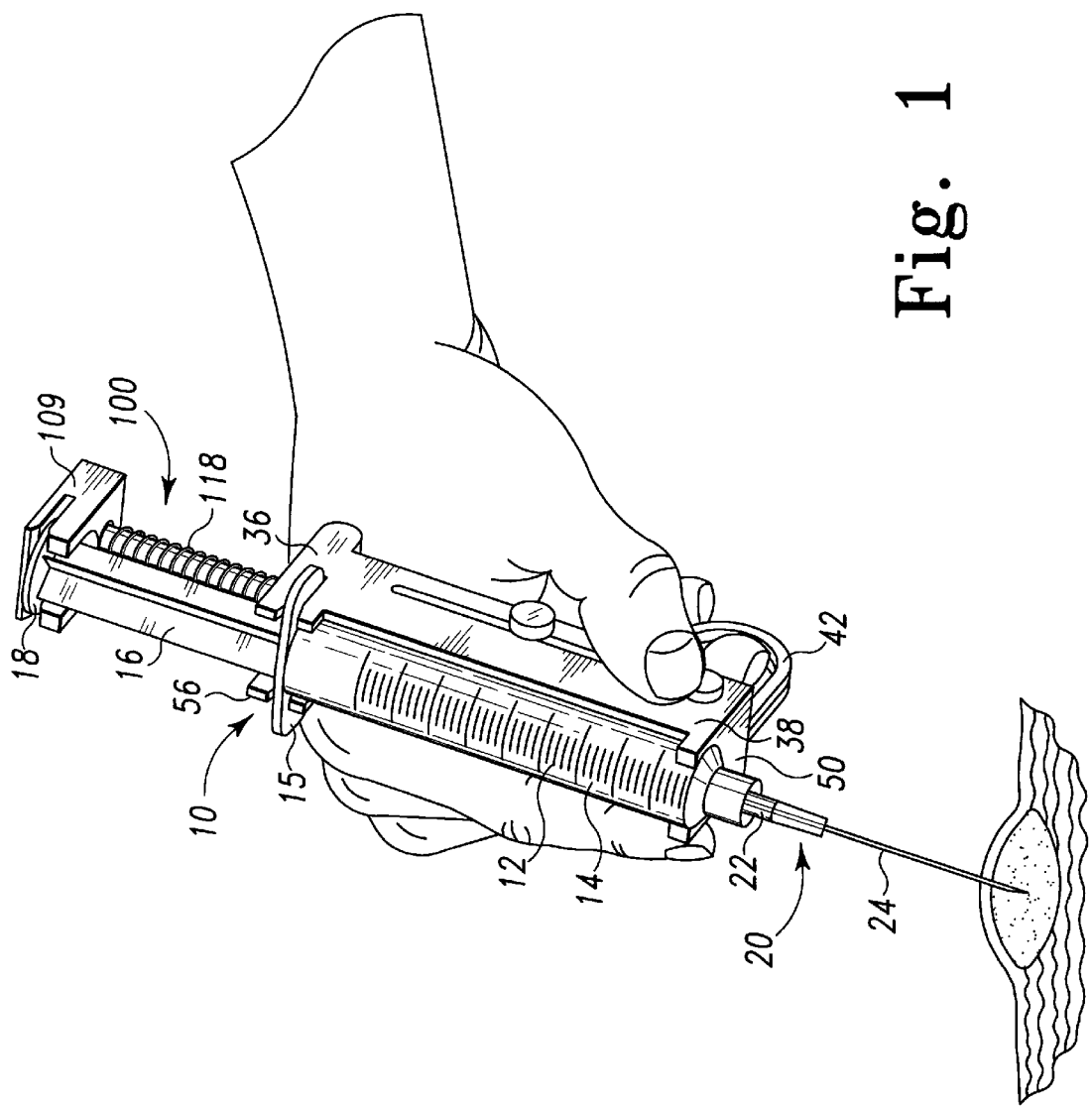
FIG. 1 is a perspective view of a pencil-grip fine needle aspiration syringe holder representing the present invention, depicted with a syringe and held in a hand of an operator.
Figure 2:
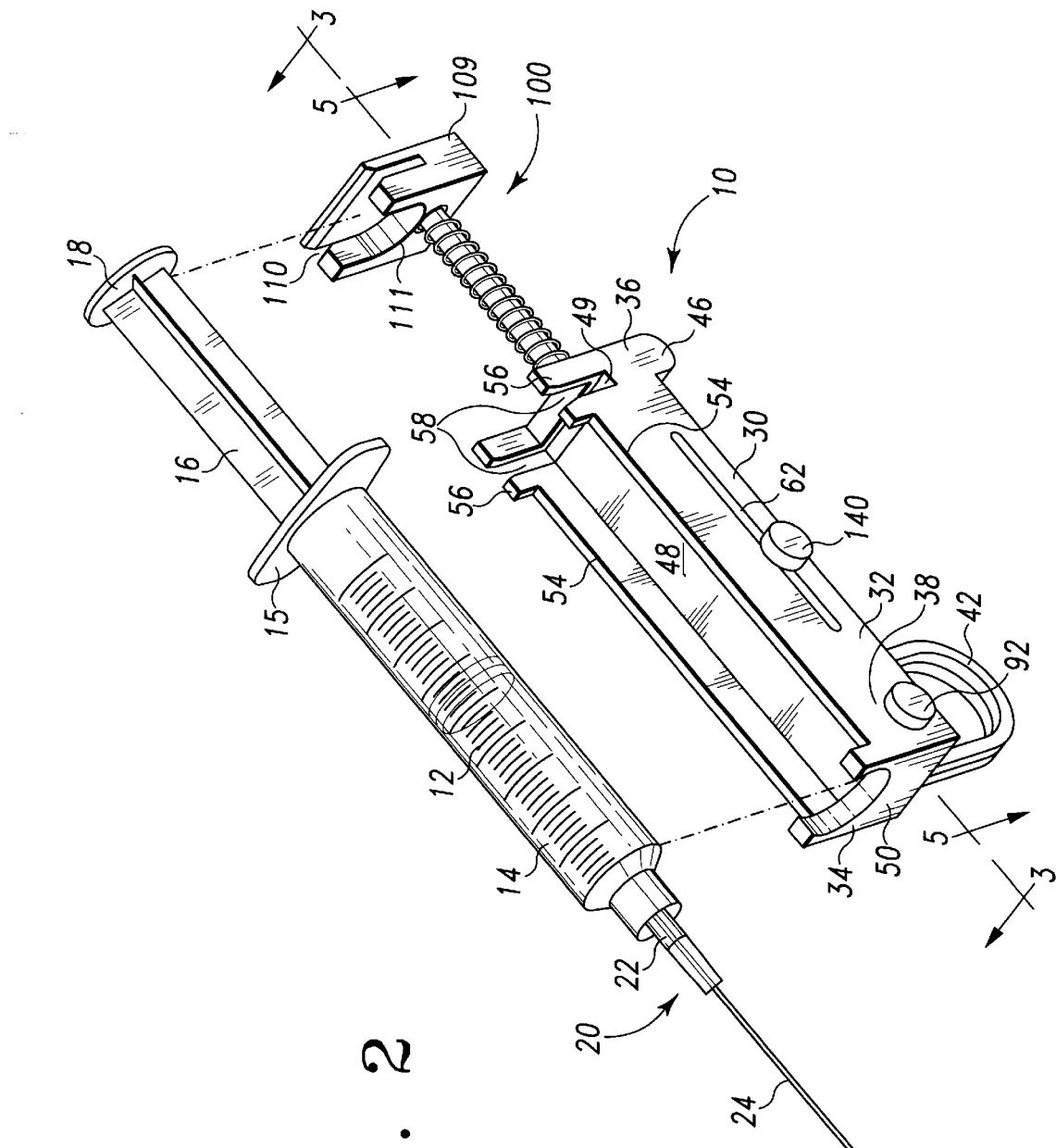
FIG. 2 is a perspective view of a pencil-grip fine needle aspiration syringe holder representing the present invention, depicted with a syringe prior to mounting to the present invention.

Referring now to the drawings for a detailed description of the present invention, reference is first made to FIGS. 1–2, generally depicting a fine needle aspiration syringe holder 10 of the present invention. As may be used with the present invention, syringe 12 is of a well-known type, preferably of 10 cc capacity, and includes barrel 14, grip 15, plunger 16 including handle 18, and needle assembly 20 disposed generally opposing handle 18. Plunger 16 is slidably movable within barrel 14 between a compact position and an extended position. Needle assembly 20 may include hub 22 formed of transparent or translucent material, and may utilize 22 gauge or narrower fine needle 24 that is typically 2.0 to 4.0 centimeters in length. Holder 10 includes generally elongated body 30 formed of left and right body halves 32 and 34, joined together, for instance, by sonic welding where body 30 is formed of a polymeric material, and is capable of receiving barrel 14 of syringe 12. Holder 10 has first end 36 and second end 38, and is adapted to be held in the manner of a pencil disposed between a thumb and forefinger as shown in FIG. 1, with first end 36 proximate to handle 18 and second end 38 proximate to needle 24. Ring-like finger engaging member 42 may be mounted to lower wall 44 of body 30 as illustrated in FIGS. 3–6, proximate to second end 38, for facilitating the grasping of holder 10 in a pencil-grip manner as illustrated in FIG. 1, and bezel 46 may be mounted to lower wall 44 proximate to first end 36. Upper wall 48 of body 30 includes upper wall stepped slot 49 and is mounted to arcuate, transverse front wall 50, rear wall 52 as illustrated in FIGS. 3–6, and a pair of longitudinal, opposing side walls 54. Each side wall 54 includes a stepped portion 56 proximate to upper wall stepped slot 49, with the stepped portions 56 defining a chamfered transverse slot 58. Body 30 defines interior chamber 60 between upper wall 48, front wall 50, rear wall 52 and side walls 54 as shown in FIGS. 3–6. Longitudinal slot 62 is defined through one of side walls 54, and slide orifice 64 is defined through rear wall 52 as illustrated in FIGS. 3–6.

As depicted in FIGS. 3–8, transversely disposed within interior chamber 60 proximate to front wall 50 is block 68, defining opposing block slots 70. In addition, interior chamber 60 defines opposing guide slots 72 proximate to rear wall 52. Disposed within interior chamber 60 and mounted between guide slots 72 is guide 74, defining guide aperture 76. The diameter of guide aperture 76 may be chosen to be substantially the same as the diameter of slide orifice 64. Located within interior chamber 60 and slidably disposed within block slots 70 is catch lock 78, defining spring mounting slots 80 and catch lock aperture 82, and having release button tab 84. Catch lock aperture 82 includes larger diameter portion 86 disposed proximate to release button tab 84 and smaller diameter portion 88 disposed proximate to spring mounting slots 80. Release button 92 is disposed through release button bore 94 defined through a side wall 54 and proximate to block slots 70, and is mounted to catch lock 78 at release button tab 84. Catch lock spring 96 is disposed within interior chamber 60, between block 68 and a side wall 54, and partially within spring mounting slots 80, and bears against catch lock 78 so that release button 92 normally extends away from body 30.

Referring to FIGS. 1–8, slide 100 includes shaft 102 having interior end 104 and opposing exterior end 106 defining tapped exterior end aperture 108. Rear holder 109 defines transverse, chamfered rear holder slot 110, arcuate notch 111, and countersunk fastener hole 112, and is mounted to shaft 102 using threaded fastener 113 disposed through fastener hole 112. Shaft 102 further defines a pair of transverse shaft slots 114 proximate to interior end 104, angled tip 116, and shaft step 117 defined adjacent to angled tip 116. The maximum diameter of angled tip 116 may be chosen to be slightly smaller than the diameter of larger diameter portion 86 of catch lock 78 but larger than the diameter of smaller diameter portion 88, and the diameter of shaft step 117 may be chosen to be slightly less than the diameter of smaller diameter portion 88. Coil slide spring 118 is disposed surrounding shaft 102, with the interior diameter of slide spring 118 chosen to be slightly greater that the diameter of shaft 102, and the exterior diameter of slide spring 118 chosen to be slightly less than the diameter of slide orifice 64 and guide aperture 76, thereby permitting sliding movement of shaft 102 and slide spring 118 through slide orifice 64 and guide 74, as will be described.

Transversely and circumferentially mounted to shaft 102 within interior chamber 60 at each shaft slot 114 is a retaining ring 120. Stop 122, defining stop aperture 124 and tapped stop fastener hole 126, is disposed surrounding shaft 102 and between retaining rings 120, with the diameter of stop aperture 124 chosen to be slightly greater than the diameter of shaft 102. Stop 122 is held in place against movement along shaft 102 by retaining rings 120, by selecting the dimension of stop 122 measured along shaft 102, that is, normal to the planes defined by retaining rings 120, to be slightly less than the perpendicular distance between retaining rings 120, so that stop 122 is tightly held therebetween. Stop 122 is further mounted to shaft 102 by threaded stop fastener 128. Regulating block 132, defining regulating block aperture 134 and tapped regulating block hole 136, is disposed surrounding shaft 102 within interior chamber 60. The diameter of regulating block aperture 134 is chosen to be slightly greater than the diameter of shaft 102 but less than the exterior diameter of slide spring 118, so that shaft 102 is capable of sliding movement through regulating block 132 while slide spring 118 bears against regulating block 132. Threaded regulating fastener 138 having regulating knob 140 is provided to adjustably mount regulating block 132 to body 30, with regulating fastener 138 disposed through longitudinal slot 62 and threadably engaged within regulating block hole 136 and regulating knob 140 bearing against a side wall 54.

Figure 3:
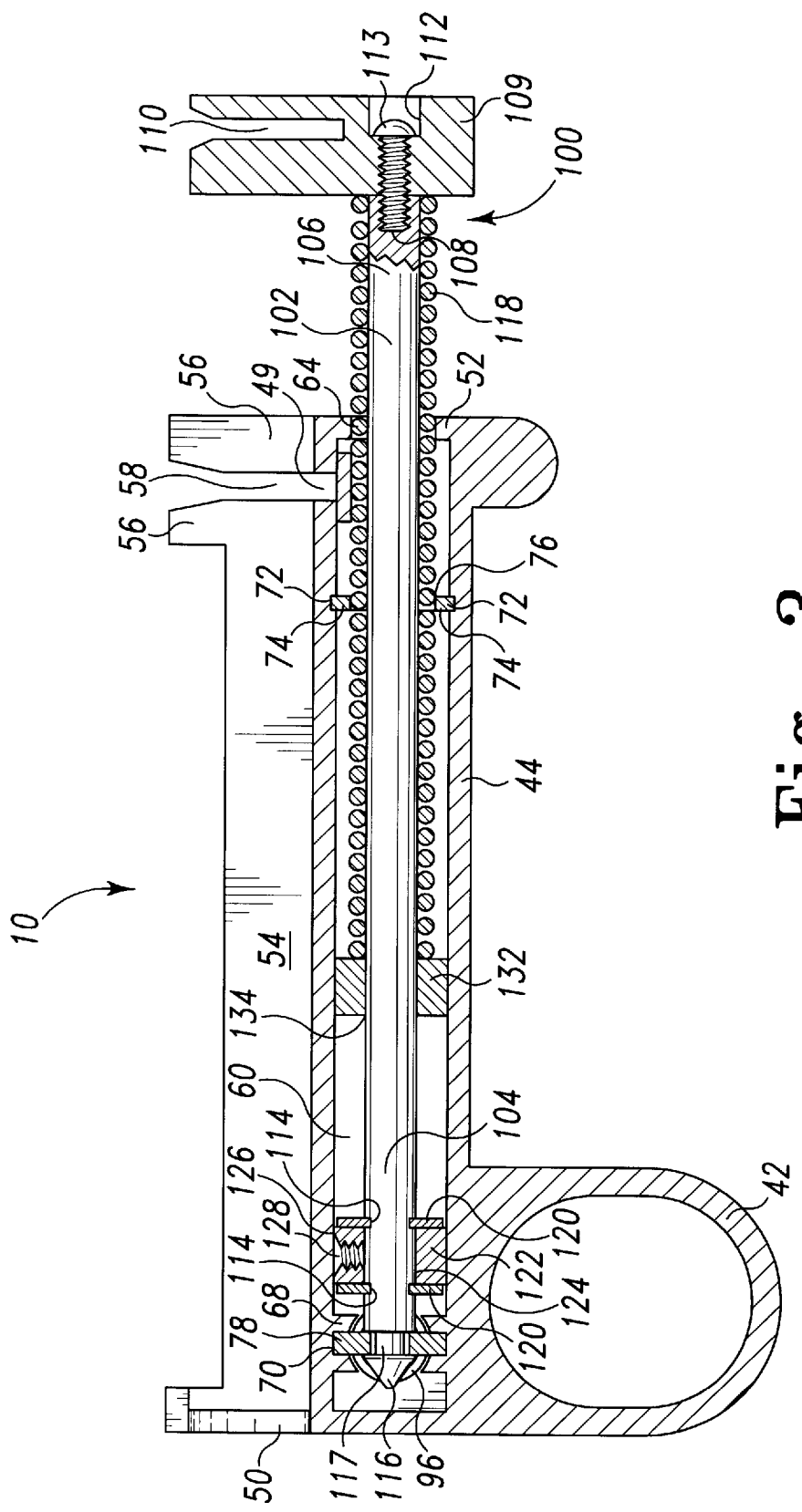
FIG. 3 is an enlarged sectional view of a pencil-grip fine needle aspiration syringe holder representing the present invention, taken along line 3—3 of FIG. 2 but depicted with the slide in the withdrawal position.
Figure 4:
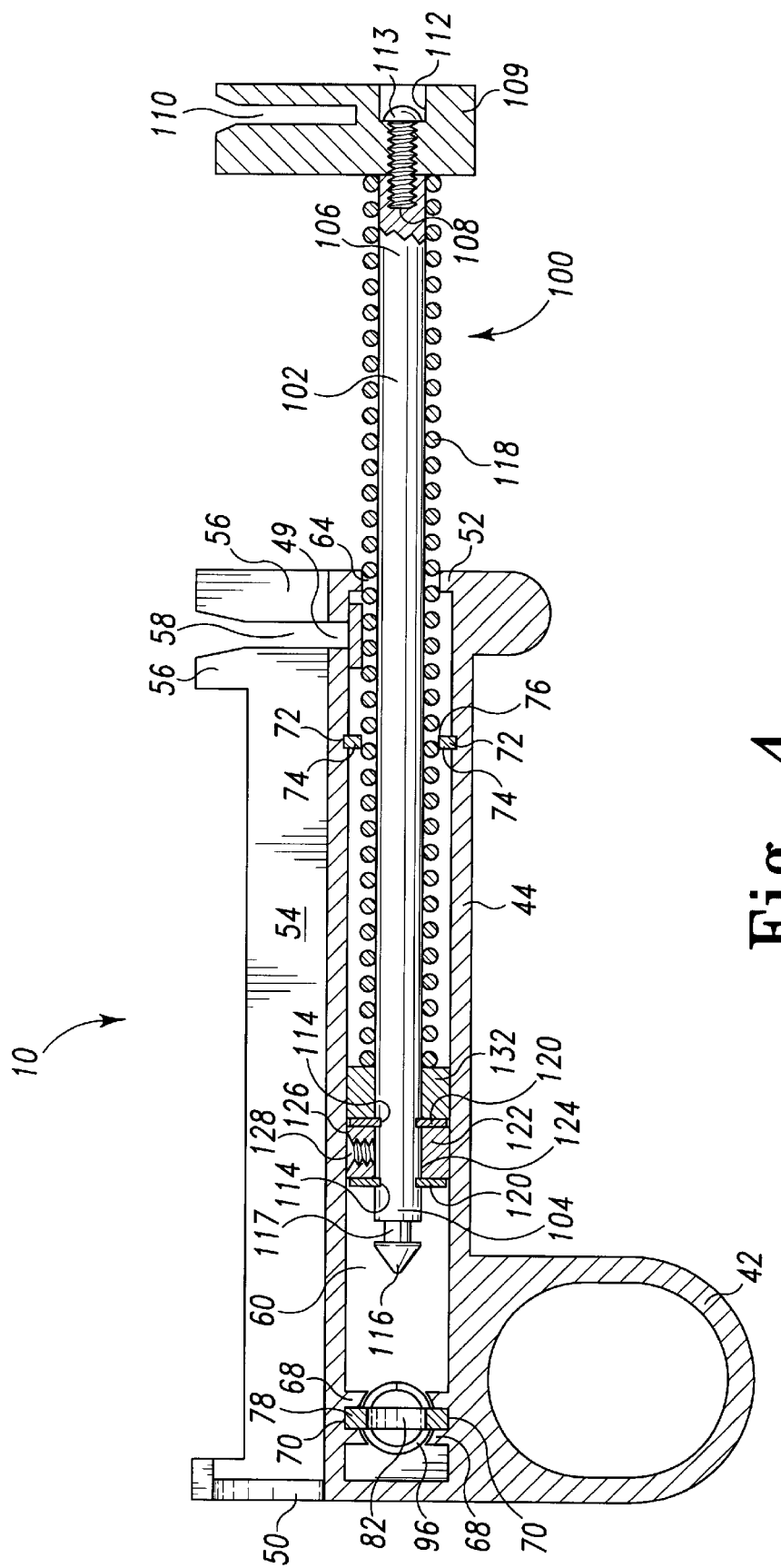
FIG. 4 is an enlarged sectional view of a pencil-grip fine needle aspiration syringe holder representing the present invention, taken along line 3—3 of FIG. 2 but depicted with the slide in the released position.
Figure 5:
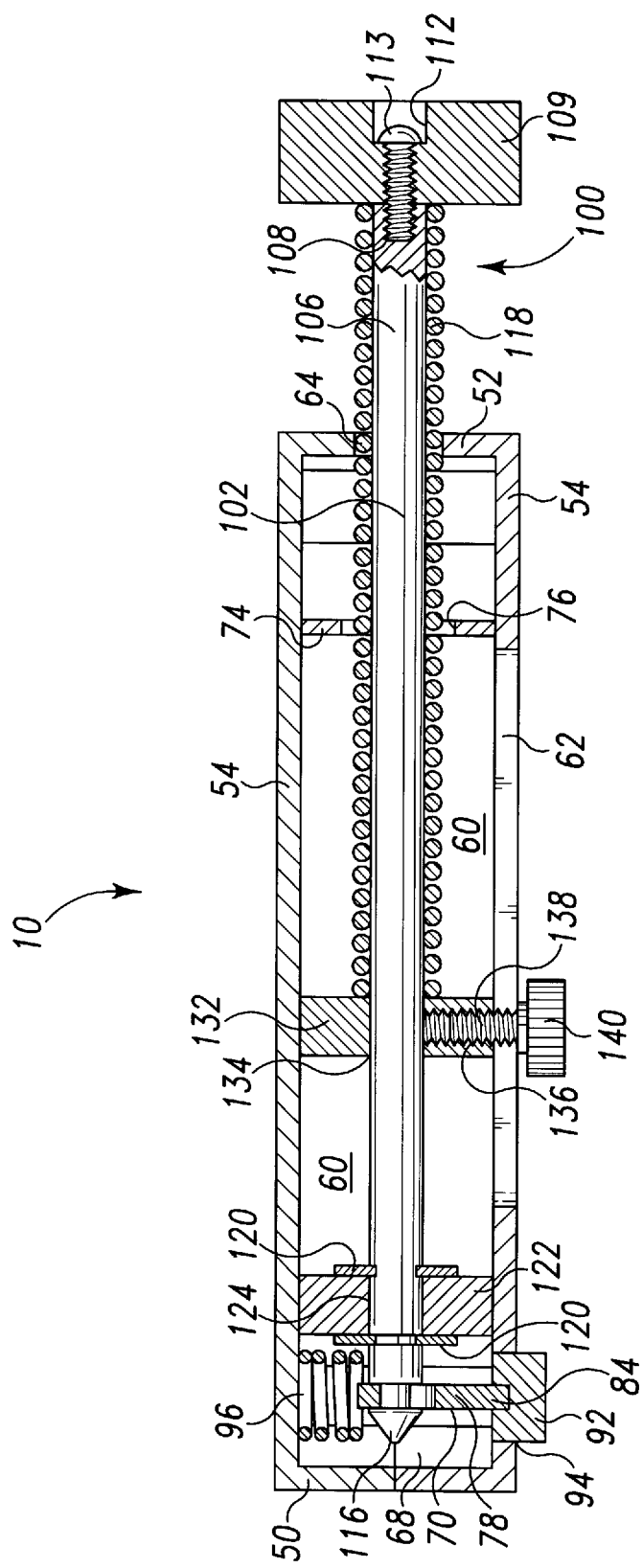
FIG. 5 is an enlarged sectional view of a pencil-grip fine needle aspiration syringe holder representing the present invention, taken along line 5—5 of FIG. 2 but depicted with the slide in the withdrawal position.
Figure 6:
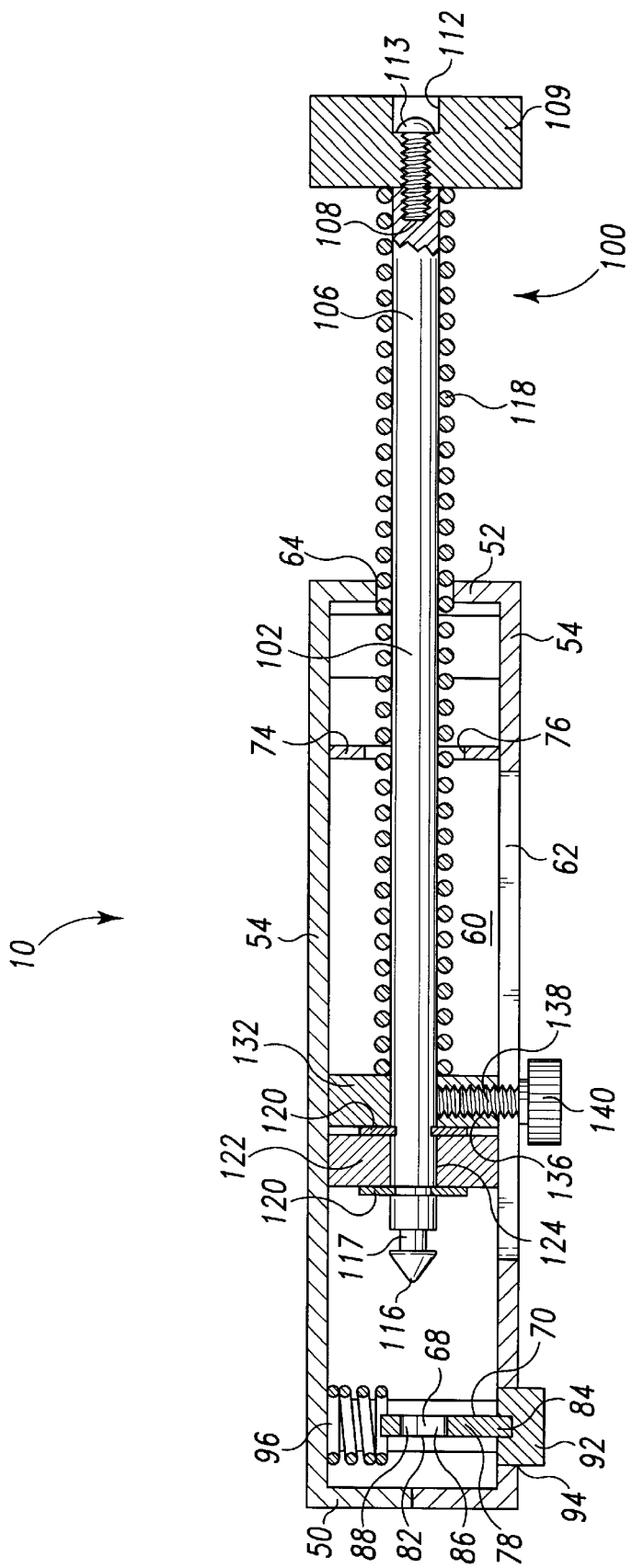
FIG. 6 is an enlarged sectional view of a pencil-grip fine needle aspiration syringe holder representing the present invention, taken along line 5—5 of FIG. 2 but depicted with the slide in the released position.
Figure 7:
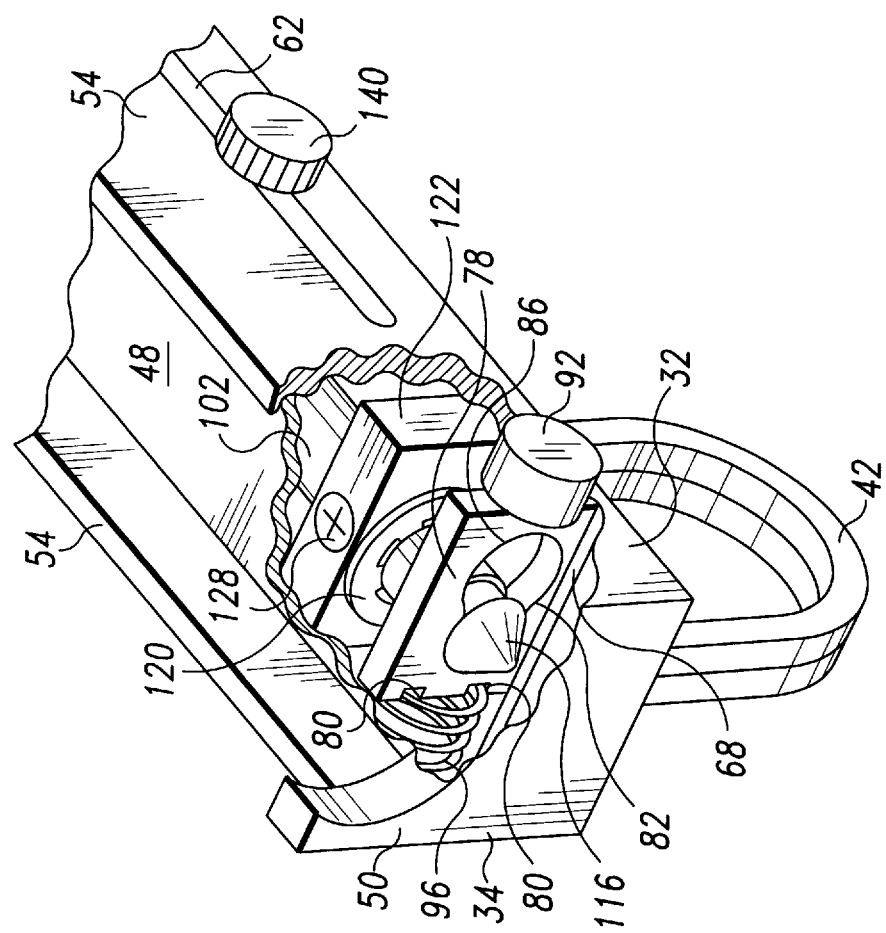
FIG. 7 is an enlarged, fragmentary, partial cut-away perspective view of a pencil-grip fine needle aspiration syringe holder representing the present invention with the slide in the withdrawal position.
Figure 8:
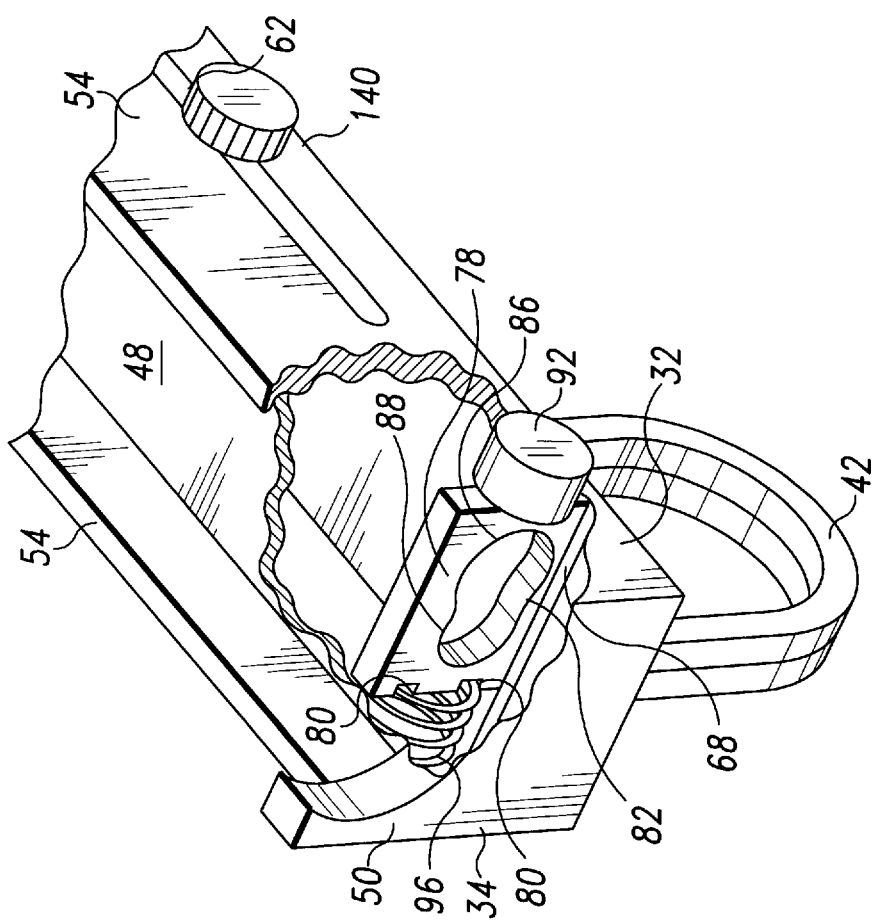
FIG. 8 is an enlarged, fragmentary, partial cut-away perspective view of a pencil-grip fine needle aspiration syringe holder representing the present invention with the slide in the released position.

Slide 100 is mounted for sliding movement with respect to body 30 between a withdrawal position where plunger 16 is disposed in a compact position, as shown in FIGS. 3, 5, and 7, and a released position where plunger 16 is disposed in an extended position, as shown in FIGS. 4, 6, and 8. Plunger 16 is biased towards the released position by a biasing member, such as slide spring 118, coupled between body 30 and slide 100 for urging slide 100 toward the released position and plunger 16 toward the extended position. It will be recognized, of course, that slide 100 may be biased towards the released position by any of a variety of biasing elements such as commonly available springs and other resilient elements.

In use, for syringe 12 of 10 cc capacity, plunger 16 may be adjusted to a compact position of approximately 2 cc and syringe 12 may be removably mounted to the present invention, with barrel 14 disposed adjacent to body 30 and through arcuate front wall 50, grip 15 disposed within transverse slot 58, and handle 18 engaged within rear holder slot 110 of rear holder 109 with plunger 16 disposed through notch 111, as shown in FIG. 1. In order for rear holder slot 110 to align with handle 18, slide 100 is pushed towards the withdrawal position as shown in FIGS. 3, 5, and 7 against the urging of slide spring 118. As interior end 104 of shaft 102 approaches catch lock 78, angled tip 116 partially enters smaller diameter portion 88 which is aligned with shaft 102 due to the biasing action of catch lock spring 96. As slide 100 is pushed further towards the withdrawal position, against the urging of slide spring 118, angled tip 116 exerts transverse force on catch lock 78 at smaller diameter portion 88 causing catch lock 78 to slide within block slots 70 against the urging of catch lock spring 96 and towards release button bore 94, so that larger diameter portion 86 becomes aligned with shaft 102. Upon alignment of shaft 102 with larger diameter portion 86, continued force exerted on slide 100 towards the withdrawal position causes angled tip 116 to slide entirely through catch lock 78, whereupon, as shaft step 117 is disposed through larger diameter portion 86, the biasing force of catch lock spring 96 causes catch lock 78 to slide within block slots 70 away from release button bore 94 so that smaller diameter portion 88 of catch lock 78 aligns with shaft 102. As the diameter of smaller diameter portion 88 has been chosen to be less than the maximum diameter of angled tip 166, shaft 102 and slide 100 are thereby locked in place, in the withdrawal position as shown in FIGS. 3, 5, and 7 with smaller diameter portion 88 of catch lock 78 in contact with shaft step 117. As a result, catch lock 78 operates to restrain slide 100 in the withdrawal position and thereby restrain plunger 16 in the compact position. It will be noted that urging of slide 100 towards the withdrawal as described, position may be facilitated by grasping the present invention in one hand, with the base of the hand pressing against rear holder 109 and one or more fingers disposed around bezel 46, and squeezing rear holder 109 towards body 30.

Referring to FIG. 1, the present invention may be held in one hand as so illustrated, with the thumb pressing against one side wall 54 adjacent to release button 92 and the index and middle fingers pressing against the opposing side wall 54, and with the ring finger disposed through finger engaging member 42 and against the little finger, so that the present invention is held in a "pencil" grip. With the present invention held in the manner described, an operator may insert needle 24 into a desired region to be aspirated, using the efforts of one hand, thereby freeing the other hand to stabilize the region to be aspirated. Using fine motor control available when holding the present invention in a pencil-grip, placement and movement of needle 24 may be precisely and accurately controlled.

Upon depression of release button 92, for instance by pinching pressure exerted by the tip of the thumb, catch lock 78 slides transversely within block slots 70 against the urging of catch lock spring 96, so that larger diameter portion 86 of catch lock 78 slides into alignment with shaft 102. As the maximum diameter of angled tip 116 is less than larger diameter portion 86, shaft 102 and slide 100 are capable of movement toward the released position as a result of urging of slide spring 118. Clearly, with release button 92 capable of operation by a finger disposed proximate to second end 38 and needle 24, release button 92 acts to release catch lock 78, allowing slide 100 to move away from the withdrawal position and towards the released position under influence of biasing force of slide spring 118, thereby moving plunger 16 from the compact position toward the extended position and decreasing pressure within syringe 12. With needle 24 placed as desired, aspiration of material from the region may be initiated by using the thumb, in a slight movement, to depress release button 92 without significantly moving other portions of the hand, thereby maintaining control of the present invention while plunger 16 is drawn back with respect to syringe 12, creating negative pressure within syringe 12 and causing aspiration of material located near tip of needle 24. Using fine motor control of the hand and wrist, the present invention may be advantageously slightly moved back and forth in an up-and-down movement within the region to be aspirated, thereby freeing additional material for aspiration. After movement of plunger 16 has stopped, aspiration is complete, and the present invention, syringe 12 and needle 24 are pulled away from the aspirated region, whereupon aspirated material present within the needle hub of the syringe 12 may be removed and analyzed as desired.

As slide 100 moves toward the released position under urging of slide spring 118, stop 122 slides within interior chamber 60 towards first end 36, as stop 122 is mounted to shaft 102 by retaining rings 120 and stop fastener 128. Sliding movement of stop 122 towards first end 36, and hence movement of slide 100 towards the released position, is limited by regulating block 132. For the reasons that regulating block 132 is disposed surrounding shaft 102 and the diameter of regulating block aperture 134 is slightly greater than the diameter of shaft 102, shaft 102 slides through regulating block 132 until stop 122 comes into contact with regulating block 132. In this way, stop 122 and regulating block 132 act as a limit member situated to intercept slide 100 between the compact position and the extended position, limiting movement of slide 100 and plunger 16, and thereby also limiting the low pressure achievable within syringe 12 for aspiration.

The extent of sliding movement permitted to slide 100 upon release of catch lock 78 by depressing release button 92 is governed by the location of regulating block 132 with respect to longitudinal slot 62. Regulating block 132 may be moved to a desired location along longitudinal slot 62 by loosening threaded regulating fastener 138 using regulating knob 140, sliding regulating block 132 to the desired location along longitudinal slot 62, and tightening regulating knob 140 to bear against a side wall 54. As a result, regulating fastener 138 with regulating knob 140 act as an adjustable regulating member coupled to regulating block 132, for adjusting the position of regulating block 132 relative to body 30, thereby controlling the degree of low pressure achievable within syringe 12 for aspiration.

The present invention having been described in its preferred embodiment, it is clear that the present invention is susceptible to numerous modifications and embodiments within the ability of those skilled in the art and without the exercise of the inventive faculty. Accordingly, the scope of the present invention is defined as set forth by the scope of the following claims.

What is claimed is:

1. A holder for a fine needle aspiration syringe, the syringe having a barrel and a plunger including a handle, the plunger movable within the barrel between a compact position and an extended position, the holder comprising:

a body for receiving the barrel;

a slide movably mounted with respect to the body for engaging the handle, capable of movement between a withdrawal position where the plunger is disposed in the compact position and a released position where the plunger is disposed in the extended position; and a biasing member coupled between the body and the slide for urging the slide toward the released position and the plunger toward the extended position.

2. The holder of claim 1, further comprising:

a catch for restraining the slide in the withdrawal position and plunger in the compact position; and a release for releasing the catch to allow the slide to move away from the withdrawal position and towards the released position under influence of the biasing member, thereby moving the plunger from the compact position toward the extended position and decreasing pressure within the syringe.

3. The holder of claim 2 further comprising a limit member situated to intercept the slide between the compact position and the extended position for limiting movement of the slide and the plunger toward the extended position, thereby limiting the low pressure achievable within the syringe.

4. The holder of claim 3 further comprising an adjustable regulating member coupled to the limit member for adjusting the position of the limit member relative to the body thereby adjusting the low pressure achievable within the syringe.

5. A holder for a fine needle aspiration syringe, the syringe having a barrel and a plunger including a handle, the plunger movable within the barrel between a compact position and an extended position, the holder comprising:

a body for receiving the barrel;

a slide movably mounted with respect to the body for engaging the handle, capable of movement between a withdrawal position where the plunger is disposed in the compact position and a released position where the plunger is disposed in the extended position;

a finger engaging member fixed to the body for facilitating the grasping of the holder in a pencil-grip manner; and a biasing member coupled between the body and the slide for urging the slide toward the released position and the plunger toward the extended position.

6. The holder of claim 5, further comprising:

a catch for restraining the slide in the withdrawal position and plunger in the compact position; and a release for releasing the catch to allow the slide to move away from the withdrawal position and towards the released position under influence of the biasing member, thereby moving the plunger from the compact position toward the extended position and decreasing pressure within the syringe.

7. The holder of claim 6 further comprising a limit member situated to intercept the slide between the compact position and the extended position for limiting movement of the slide and the plunger toward the extended position, thereby limiting the low pressure achievable within the syringe.

8. The holder of claim 7 further comprising an adjustable regulating member coupled to the limit member for adjusting the position of the limit member relative to the body thereby adjusting the low pressure achievable within the syringe.

9. A holder for a fine needle aspiration syringe, the syringe having a barrel, a plunger including a handle, and a needle disposed generally opposing the handle, the plunger movable within the barrel between a compact position and an extended position, the holder comprising:

a generally elongated body for receiving the barrel, having a first end and a second end, and adapted to be held in the manner of a pencil between a thumb and forefinger with the first end proximate to the handle and the second end proximate to the needle;

a slide movably mounted with respect to the body for engaging the handle, capable of movement between a withdrawal position where the plunger is disposed in the compact position and a released position where the plunger is disposed in the extended position; and a biasing member coupled between the body and the slide for urging the slide toward the released position and the plunger toward the extended position.

10. The holder of claim 9, further comprising:

a catch for restraining the slide in the withdrawal position and plunger in the compact position; and a release disposed proximate to the second end for releasing the catch to allow the slide to move away from the withdrawal position and towards the released position under influence of the biasing member, thereby moving the plunger from the compact position toward the extended position and decreasing pressure within the syringe, the release capable of operation by a finger disposed proximate to the second end.

11. The holder of claim 10 further comprising a limit member situated to intercept the slide between the compact position and the extended position for limiting movement of the slide and the plunger toward the extended position, thereby limiting the low pressure achievable within the syringe.

12. The holder of claim 11 further comprising an adjustable regulating member coupled to the limit member for adjusting the position of the limit member relative to the body thereby adjusting the low pressure achievable within the syringe.

13. A holder for a fine needle aspiration syringe, the syringe having a barrel, a plunger including a handle, and a needle disposed generally opposing the handle, the plunger movable within the barrel between a compact position and an extended position, the holder comprising:

a generally elongated body for receiving the barrel, having a first end and a second end, and adapted to be held in the manner of a pencil between a thumb and forefinger with the first end proximate to the handle and the second end proximate to the needle;

a slide movably mounted with respect to the body for engaging the handle, capable of movement between a withdrawal position where the plunger is disposed in the compact position and a released position where the plunger is disposed in the extended position;

a finger engaging member fixed to the body for facilitating the grasping of the holder in a pencil-grip manner; and a biasing member coupled between the body and the slide for urging the slide toward the released position and the plunger toward the extended position.

14. The holder of claim 13, further comprising:

a catch for restraining the slide in the withdrawal position and plunger in the compact position; and a release disposed proximate to the second end for releasing the catch to allow the slide to move away from the withdrawal position and towards the released position under influence of the biasing member, thereby moving the plunger from the compact position toward the extended position and decreasing pressure within the syringe, the release capable of operation by a finger disposed proximate to the second end.

15. The holder of claim 14 further comprising a limit member situated to intercept the slide between the compact position and the extended position for limiting the outward movement of the slide and plunger thereby limiting the low pressure achievable within the syringe.

16. The holder of claim 15 further comprising an adjustable regulating member coupled to the limit member for adjusting the position of the limit member relative to the body thereby adjusting the low pressure achievable within the syringe.

* * * * *